United States Patent [19]

Szarka et al.

[11] 4,250,258
[45] Feb. 10, 1981

[54] USE OF PHENOXYALKANES AS PRECURSORS IN PENICILLIN V FERMENTATION

[75] Inventors: Laszlo J. Szarka, East Brunswick; Robert W. Eltz, Princeton, both of N.J.

[73] Assignee: E. R. Squibb & Sons, Inc., Princeton, N.J.

[21] Appl. No.: 105,801

[22] Filed: Dec. 20, 1979

[51] Int. Cl.$^3$ ............................................. C12P 37/04
[52] U.S. Cl. ...................................... 435/45; 435/935
[58] Field of Search ............................. 435/43, 45, 46

[56] References Cited

U.S. PATENT DOCUMENTS

| 2,440,360 | 4/1948 | Behrens et al. | 435/46 |
| 2,562,410 | 7/1951 | Behrens et al. | 435/43 |

FOREIGN PATENT DOCUMENTS 49-28432  7/1974  Japan .

OTHER PUBLICATIONS

Science vol. 106, pp. 503–505 (1947).
Demain, Biosynthesis of Antibiotics, pp. 30–42 (1966).
Perlman, Chemically Defined Media for Antibiotics Production, Annals of N.Y. Academy of Sciences, vol. 139, pp. 258–269 (1966).
Pidoplichko et al., Chem. Abst., vol. 71, p. 46903r.
Avanzini et al., Annals N.Y. Academy of Sciences vol. 153, pp. 534–540 (1968).
Niedermayer, Analytical Chemistry, vol. 36, pp. 938–939 (1964).
Webley et al., Nature, vol. 178, pp. 1467–1468 (1956).
Davis et al., Applied Microbiology, vol. 9, pp. 383–388 (1961).
Davis, Petroleum Microbiology, pp. 327–331 (1967).

*Primary Examiner*—Alvin E. Tanenholtz
*Attorney, Agent, or Firm*—Lawrence S. Levinson; Stephen B. Davis

[57] ABSTRACT

Penicillin V is prepared by culturing a penicillin-producing microorganism in a medium containing suitable sources of nitrogen, carbon and energy, and inorganic salts. One or more phenoxyalkanes of the formula

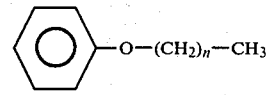

wherein n is an integer from 6 to 13 are included within the medium as the sidechain precursor.

8 Claims, No Drawings

USE OF PHENOXYALKANES AS PRECURSORS IN PENICILLIN V FERMENTATION

BACKGROUND OF THE INVENTION

Penicillin V, i.e., 3,3-dimethyl-7-oxo-6-[(phenoxyacetyl)amino]-4-thia-1-azabicyclo[3.2.0]-heptane-2-carboxylic acid, also known as phenoxymethyl penicillin, is a widely prescribed anti-bacterial agent. Penicillin V is available in the free acid or various salt forms such as the potassium salt and is formulated primarily for oral administration in tablets or solutions.

Penicillin V is conventionally prepared by fermentation. A penicillin producing microorganism is cultured in a medium containing a source of nitrogen, a source of carbon and energy, various inorganic salts, and a sidechain precursor. Phenoxyacetic acid and its salts such as potassium phenoxyacetic acid are conventionally employed as Penicillin V sidechain precursors. 2-Phenoxyethanol has also been employed as a Penicillin V sidechain precursor, Brandl et al., Wien Med. Wochenschr. 1953, p 602. N-(2-(Hydroxyethyl)phenoxyacetamide has also been employed as a Penicillin V sidechain precursor, the Editorial Board of the Monograph on the Chemistry of Penicillins, Science, Vol. 106, p. 503–505.

Nara et al. in Japanese Pat. No. 28432 (1974) disclose producing benzylpenicillin or Penicillin V in a fermentation medium containing n-paraffins as the carbon source and phenylacetic acid or phenoxyacetic acid as the sidechain precursor.

Similarly, Pidoplichko et al., Chem. Abst., Vol. 71, p. 46903r, disclose that Penicillium species are able to use hydrocarbons, hexadecane, higher secondary alcohols, $C_{17-20}$ fatty acids, and higher paraffins as the sole source of carbon.

SUMMARY OF THE INVENTION

This invention is directed to the fermentative production of Penicillin V. A penicillin-producing microorganism is cultured in a medium containing suitable sources of nitrogen, carbon and energy, and inorganic salts. The medium also includes as the sidechain precursor one or more phenoxyalkanes of the formula

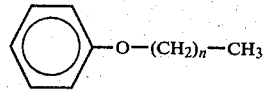

wherein n is an integer from 6 to 13.

DETAILED DESCRIPTION

This invention is directed to producing Penicillin V by a conventional fermentative biosynthetic process except that one or more phenoxyalkanes of the formula

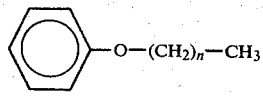

wherein n is an integer from 6 to 13 is included within the fermentation medium as the sidechain precursor.

By the term "conventional fermentation process" it is meant that the process conditions, the penicillin-producing microorganism, the nitrogen source, the carbon and energy source, and the salts present within the culture medium are those commonly employed in the production of Penicillin V.

Suitable nitrogen sources for inclusion within the culture medium include various inorganic or organic salts or compounds such as urea, liquid ammonia, or ammonium salts such as ammonium chloride, ammonium sulfate, ammonium nitrate, ammonium acetate, ammonium phosphate, etc., and mixtures thereof. Cornsteep liquor, which is a mixtures of various nitrogen sources and inorganic compounds, is a preferred component of the culture medium.

Suitable carbon and energy sources for inclusion within the culture medium include carbohydrates such as lactose, glucose, sucrose, etc., and mixtures thereof. Other materials which can be employed include ethanol and various n-paraffins. A fatty oil such as lard oil, peanut oil, corn oil, etc., can also be included within the culture medium as taught by Perlman in U.S. Pat. No. 2,641,567.

Suitable inorganic salts for inclusion within the culture medium include magnesium sulfate, sodium phosphate, sodium nitrate, potassium monohydrogen phosphate, potassium dihydrogen phosphate, iron sulfate, manganese chloride, calcium chloride, calcium carbobate, sodium chloride, zinc sulfate, etc., and mixtures thereof.

Culturing is conducted under aerobic conditions, such as aerobic shaking of the culture or aeration of a submerged culture with agitation. The temperature employed can vary from about 20° C. to about 30° C. and the pH can be from about 5.0 to 7.5. Culturing is generally carried out for from about 5 to about 14 days. The resulting Penicillin V is separated from the culture medium by conventional techniques such as extraction and crystallization procedures.

This process can employ various penicillin producing cultures. In general those of the Penicillium type are preferred, with *Penicillium chrysogenum* being most preferred.

The phenoxyalkane sidechain precursors can be employed in this process in a similar manner to the phenoxyacetic acid salts. Thus, the phenoxyalkane or mixture of phenoxyalkanes can be added periodically in small amounts to the culture medium during the course of the fermentation process.

Preferably, the phenoxyalkanes employed in this process are one or more wherein n is an integer from 7 to 11. Most preferred are those wherein n is 8 or 9. These most preferred phenoxyalkanes are less toxic to the penicillin producing microorganisms than the commercially employed potassium phenoxyacetic acid. Consequently, these most preferred phenoxyalkanes can be added in toto to the initial culture medium, thus eliminating the need for careful monitoring of the medium and the periodic introduction of additional sidechain precursor.

The following examples are illustrative of the invention.

EXAMPLES 1 and 2

The following examples demonstrate Penicillin V production achieved in fermentations employing various phenoxyalkane sidechain precursors as compared with a control (no sidechain precursor) fermentation. All of these fermentations employed the following culture medium:

|  | gram/liter in water |
| --- | --- |
| Lactose | 90 |
| Cornsteep liquor | 60 |
| $(NH_4)_2SO_4$ | 5 |
| $NaNO_3$ | 2 |
| $CaCO_3$ | 6 |
| $NaH_2PO_4$ | 4 |
| Lard Oil | 3 |
| $MgSO_4 \cdot 7H_2O$ | 0.25 |
| $MnSO_4 \cdot 4H_2O$ | 0.025 |
| $ZnSo_4 \cdot 7H_2O$ | 0.025 |

The penicillin-producing microorganism employed in these fermentations is *Pencillium chrysogenum* ATCC 20444 which is a known penicillin-producing culture publically available from the American Type Culture Collection, Rockville, Maryland.

The fermentations are performed as follows. 25.2 Liters of the above culture medium is sterilized in a 38 liter capacity fermentor. The fermentor is a stainless steel tank with a 300 mm. inner diameter equipped with three six-bladed turbo impellers. The tank is operated at 25° C. with sterile air supply at a final maximum rate of 2.5 vol./vol./min., and an agitator speed of 700 rpm. This speed is varied according to the foaming conditions in the tank. The fermentor is inoculated with 2.5 liters of 38 hour old broth culture of *Penicillium chrysogenum* ATCC 20444. The pH of the broth is controlled between 5.5 and 7.3 using 50% sodium hydroxide solution. The volume of the batch is maintained at 25 liters by the addition of sterile water every 12 hours.

In Example 1 225 g. of the phenoxydecane sidechain precursor is added to the fermentor initially and in Example 2 210 g. of the phenoxynonane sidechain precursor is added to the fermentor initially.

In one control experiment phenoxyacetic acid solution is used as the sidechain precursor. The fermentation parameters are the same as mentioned above. The phenoxyacetic acid is dissolved at alkaline pH to produce a 20% wt./vol. solution which is added to the broth at a rate of 75 ml./24 hours.

In another control experiment no sidechain precursor is added.

The fermentations are performed for a given length of time after which the penicillin potency is determined in the broth by the hydroxylamine method. (Avanzini et al., Ann. N.Y. Acad. Sci., Vol. 153, p. 534–540) The phenoxyacetic acid concentration in the broth is also determined. (Niedermayer, Anal. Chem., Vol. 36, p. 938–939)

The presence of Penicillin V in the fermentation broth is confirmed by a bioautogram technique. In this procedure, a sample of the fermentation broth is spotted on chromatographic paper along with other standard samples which contain known amounts of Penicillin V and Penicillins K, F, G and X. The spots are developed and plated on an agar bioautographic plate which has been treated with *Staph. aureus*. The plate is incubated overnight. The zones of inhibition are measured and compared with the standards. By this procedure, the presence of Penicillin V in the fermentation broth is confirmed and the percentage of other penicillins within the broth can be determined.

The data obtained are summarized in the following table.

| Example | 1 | 2 | Control | Control |
| --- | --- | --- | --- | --- |
| Precursor | Ph—O—$(CH_2)_9$—$CH_3$ | Ph—O—$(CH_2)_8$—$CH_3$ | Ph—O—$CH_2COOH$ | None |
| Length of Fermentation | 142 hours | 144 hours | 144 hours | 144 hours |
| Penicillin Potency (expressed as Pen V units/ml.) | 7120 | 7110 | 7060 | 2900 |
| Phenoxyacetic Acid in the broth at harvest (mg./ml.) | 0.70 | 0.26 | 1.4 | 0 |
| Percentage of Pen V to total penicillins (by bioautograph) | >95% | >97% | >90% | Mixture of penicillin K, F and X with trace amount of Pen G. |

What is claimed is:

1. The fermentative method of producing Penicillin V which comprises aerobically culturing a penicillin-producing microorganism in a medium containing a source of nitrogen, a source of carbon and energy, inorganic salts, and as the sidechain precursor one or more phenoxyalkanes of the formula

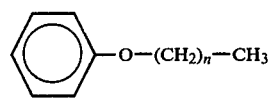

wherein n is an integer from 6 to 13, said fermentation process being performed without the addition of phenoxyacetic or its salts to said medium, followed by the step of recovering the Penicillin V from said medium.

2. The method of claim 1 wherein the penicillin-producing microorganism is of the Penicillium genus.

3. The method of claim 2 wherein the medium is at a temperature of from about 20° C. to about 30° C., the pH is at from about 5 to about 7.5, and the culturing is carried out for from about 5 to about 14 days.

4. The method of claim 3 wherein the sidechain precursor is one or more phenoxyalkanes of the formula

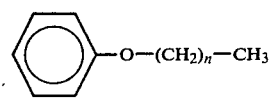

wherein n is an integer from 7 to 11.

5. The method of claim 4 wherein the sidechain precursor is one or more phenoxyalkanes of the formula

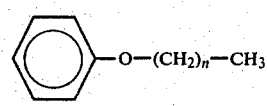
wherein n is 8 or 9.
6. The method of claim 5 wherein the penicillin-producing microorganism is a strain of *Penicillium chrysogenum*.
7. The method of claim 6 wherein the sidechain precursor is
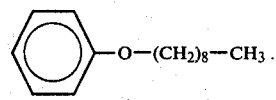
8. The method of claim 6 wherein the sidechain precursor is
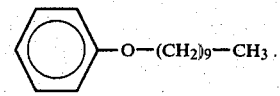
* * * * *